United States Patent [19]
Uppal et al.

[11] Patent Number: 5,365,009
[45] Date of Patent: Nov. 15, 1994

[54] HETEROGENEOUS ALKYLATION AND REGENERATION OF ALKYLATION CATALYSTS

[75] Inventors: Ashok Uppal, Sarnia; William J. Murphy, Bright's Grove; Joseph P. Boyle, Sarnia, all of Canada

[73] Assignee: Exxon Research and Engineering Company, Florham Park, N.J.

[21] Appl. No.: 48,385

[22] Filed: Apr. 14, 1993

[51] Int. Cl.$^5$ .................... C07C 2/58; B01J 29/38; B01J 38/14
[52] U.S. Cl. .................... 585/722; 502/38; 502/52
[58] Field of Search ............ 502/34, 38, 39, 52; 585/722, 533

[56] References Cited

U.S. PATENT DOCUMENTS

| | | | |
|---|---|---|---|
| 3,655,813 | 4/1972 | Kirsch et al. | 585/722 |
| 4,165,296 | 8/1979 | Ishii et al. | 252/412 |
| 5,183,789 | 2/1993 | Boyle | 502/52 |

FOREIGN PATENT DOCUMENTS 2029719  3/1980  United Kingdom .

OTHER PUBLICATIONS

Copperthwaite, R. G.; Ozone Reactivation of a Synthetic Zeolite Catalyst for Methanol Conversion; Jan. 1985; 644–645; J. Chem. Soc. Com. 074.

Copperthwaite, R. G.; Regeneration of Pentasil Zeolite Catalysts using Ozone and Oxygen; Jul. 30, 1985; 1007–1016; J. Chem. Soc., 1986.

Hutchings, G. J.; A Comparative Study of Reactivation of Zeolite Y Using Oxygen and Ozone/Oxygen Mixtures; Applied Catalysis, 34 (1987) 153–161.

*Primary Examiner*—Paul E. Konopka
*Attorney, Agent, or Firm*—Richard D. Jordan; Roy J. Ott

[57] ABSTRACT

An alkylation process which utilizes a solid alkylation catalyst is disclosed. The catalyst, which has carbonaceous material adsorbed thereto, is regenerated by reacting the adsorbed carbonaceous material. The reaction step is accomplished by heating the catalyst in the presence of ozone to form an ozonated hydrocarbon, wherein the ozonated hydrocarbon includes carbonyl carbons. The ozonated hydrocarbon is removed by desorbing the carbonyl carbons from the solid alkylation catalyst. The carbonaceous material is preferably reacted at a temperature ranging from about 20° C. to 200° C. The ozone is preferably in a gaseous stream at a concentration ranging from about 1 to 50 volume percent. The carbonyl components are preferably desorbed from the heated alkylation catalyst by sweeping the catalyst with a desorption fluid.

12 Claims, 2 Drawing Sheets

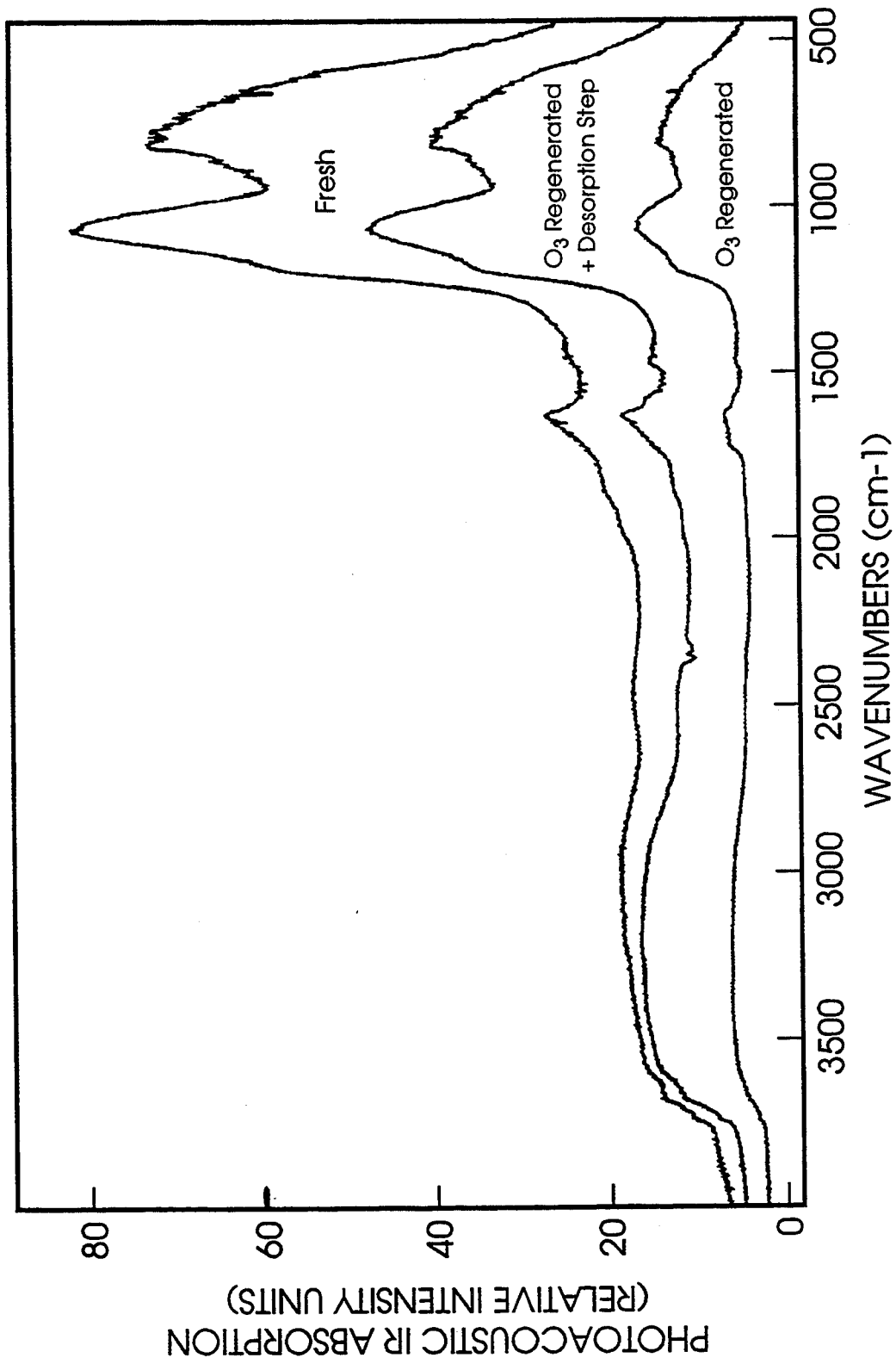

HETEROGENEOUS ALKYLATION AND REGENERATION OF ALKYLATION CATALYSTS

FIELD OF THE INVENTION

This invention relates to heterogeneous catalytic alkylation of paraffins and olefins to form higher molecular weight, high octane products. In particular, the invention relates to the catalytic alkylation of an isoparaffin with an olefin and, more particularly, to the alkylation of isobutane with an olefin having from 3 to 5 carbon atoms.

BACKGROUND OF THE INVENTION

Alkylation, as the term is commonly used in the petroleum industry, is the reaction between an olefin and a branched chain paraffin to obtain a highly branched chain paraffin having a higher molecular weight than the isoparaffin employed as the initial reactant. Commercial processes using strong mineral acid catalysts alkylate isobutane with $C_3$-$C_4$ olefins to form high octane liquid products which distill in the gasoline range, 35°-210° C.

Two well known commercial processes are in liquid phase and use strong acids, i.e., hydrofluoric (HF) and sulfuric acid ($H_2SO_4$). Although these processes have been successful from both an alkylate yield and a quality standpoint, there are some inherent disadvantages using strong acids in liquid phase. Major disadvantages are threats to operator safety and a high risk of environmental pollution as a result of accidental acid release and from spent acid disposal. This has prompted the exploration of solid catalyst processes for alkylation.

A large variety of solid catalysts, including amorphous and crystalline materials, have been demonstrated to be effective for use as alkylation catalysts. However, a major drawback of using a solid catalyst is a rapid loss in catalyst activity, thus requiring frequent regeneration of the catalyst. A number of regeneration methods including solvent wash, use of ultrasonics, conventional oxygen burn, etc. have been proposed.

Commercial alkylation processes which use solid catalysts generally incorporate an alkylation cycle and a catalyst regeneration cycle. In the alkylation cycle, the catalyst is in contact with the hydrocarbon feed. This cycle is also known as the "on-oil" portion of the operating cycle. During the on-oil portion of the operating cycle, the activity of the catalyst gradually declines due to the build-up of carbonaceous deposits, or coke, on the catalyst. During the catalyst regeneration cycle, the catalyst is taken out of contact with the hydrocarbon feed and the catalyst is regenerated.

In the semi-regenerative process, during the on-oil portion of the operating cycle, the entire unit is operated by gradually and progressively adjusting the temperature and feed rate to maintain yield and selectivity. At a predetermined activity level the entire unit is shut down for regeneration of the catalyst. After regeneration, the unit is put back in the on-oil cycle.

In a cyclic regeneration process, each individual reactor of a plurality of reactors is capable of being individually isolated. In effect, during the regeneration cycle, a reactor is swung out of line by various manifolding arrangements, such as by motor operated valving and the like. The catalyst is regenerated to remove the coke deposits while the other reactors remain on stream. A "swing reactor" temporarily replaces the reactor which is swung out of line, until regeneration of the catalyst is complete.

The net result in either type of regeneration process is, however, the same. The coke must be oxidatively burned from the catalyst at temperatures ranging from about 400° C. to about 800° C., and the higher the required temperature, inter alia, the greater the damage to the catalyst.

Attempts have been made to regenerate zeolite catalysts at low temperature, as disclosed by (1) Copperthwaite, R. G. et al., J. Chem. Soc., Chem. Commun. 1985, p 644–645; (2) Copperthwaite, R. G. et al., J. Chem. Soc., Faraday Trans. 1, 1986, 82, p 1007–1017; and (3) Hutchings, G. J. et al., Applied Catalysis, 34, 1987, p 153–161. In attempts to regenerate a 1/16 inch zeolite Y type of catalyst extrudate (LZY82®, Union Carbide), as described by Hutchings et al., upon breaking the catalyst particles, they observed a black core of coked catalyst surrounded by a white layer of partially regenerated catalyst. More carbon remained on the catalyst when it was regenerated with ozone than remained on a similar catalyst regenerated with oxygen. In the regeneration of ZSM-5 powder, as described in the two Copperthwaite et al. publications, generally similar results were obtained. It would be very advantageous, and indeed a need exists, for a low temperature process which completely regenerates coked solid alkylation catalysts to perform in a manner that is essentially equivalent to that of fresh catalyst.

SUMMARY OF THE INVENTION

In order to overcome problems inherent in the prior art and achieve a solid alkylation catalyst that is completely regenerated, the present invention provides a process for regenerating a solid alkylation catalyst having carbonaceous material adsorbed thereto. The process comprises reacting the adsorbed carbonaceous material by heating in the presence of ozone to form an ozonated hydrocarbon, wherein the ozonated hydrocarbon comprises carbonyl carbons, and removing the ozonated hydrocarbon by desorbing the carbonyl carbons from the solid alkylation catalyst.

The present invention also provides for an alkylation process, wherein an olefin and a branched chain paraffin are contacted together with a solid alkylation catalyst to form an alkylate product with carbonaceous material being adsorbed to the solid alkylation catalyst. The process comprises stopping the olefin and branched chain paraffin from contacting the solid alkylation catalyst, reacting the adsorbed carbonaceous material by heating in the presence of ozone to form an ozonated hydrocarbon, wherein the ozonated hydrocarbon comprises carbonyl carbons, removing the ozonated hydrocarbon by desorbing the carbonyl carbons from the solid alkylation catalyst, and recontacting the olefin and branched chain paraffin with the solid alkylation catalyst to form alkylate product.

BRIEF DESCRIPTION OF THE DRAWINGS

The present invention will be better understood by reference to the Description of the Preferred Embodiments when taken together with the attached drawings, wherein:

FIG. 2 shows photoacoustic IR spectra of fresh catalyst, ozone regenerated catalyst that has been regenerated without using a desorption step, and ozone regenerated catalyst that has been regenerated using a desorption step.

DETAILED DESCRIPTION OF THE PREFERRED EMBODIMENTS

Figure 1:
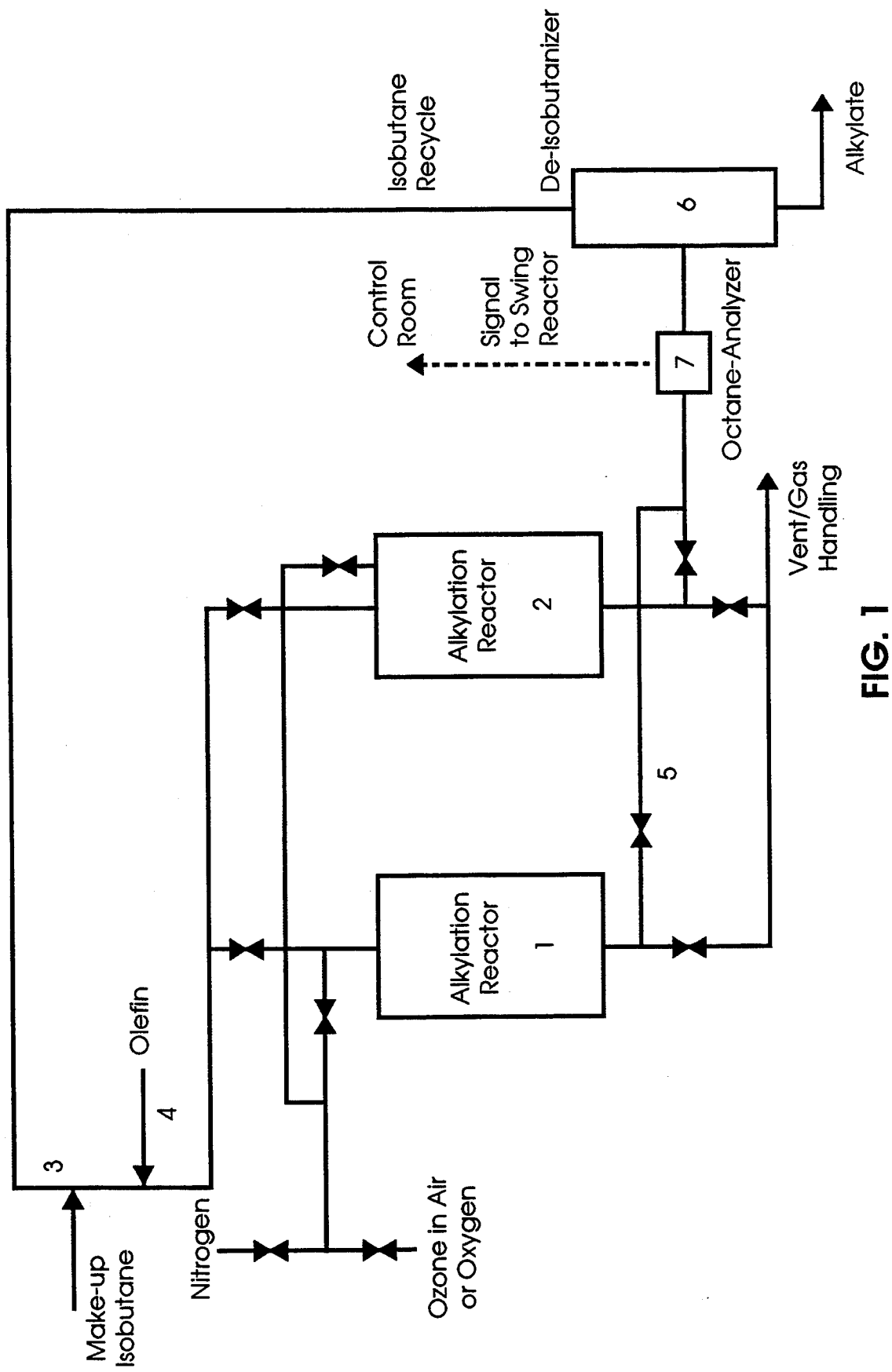
FIG. 1 shows an embodiment of the invention which includes a 2-reactor, fixed-bed system.

Alkylation, as the term is commonly used in the petroleum industry, describes the reaction between an olefin and a branched chain paraffin. The reaction process produces a highly branched paraffin having a higher molecular weight than the branched chain paraffin which was used as the initial reactant. Commercial processes using strong mineral acids, such as sulfuric or hydrofluoric acid catalysts, alkylate isobutane with $C_3$–$C_5$ olefins to form high octane liquid products which distill in the gasoline range 35°–210° C.

The present invention utilizes a solid alkylation catalyst in the alkylation process. One embodiment of the process is shown in FIG. 1, which is a flow diagram of a 2-reactor, fixed-bed system. The reactants, which are shown in FIG. 1 as a typical isobutane feed stream 3 and an olefin feed stream 4, are mixed prior to entering alkylation reactor 1, which is in the on-oil mode. The alkylation reaction occurs as the reaction mixture passes downwards through the alkylation reactor 1. The product of the alkylation reaction, a highly branched paraffin, leaves the alkylation reactor 1 through a product effluent line 5, and passes through an on-line analyzer 7. After passing through the on-line analyzer 7, the alkylate product is transported to a de-isobutanizer 6. At the de-isobutanizer 6, unreacted isobutane is separated and returned to mix with the isobutane feed stream 3 and the olefin feed stream 4.

The on-line analyzer 7 is used to continuously analyze the octane level of the alkylate product. A continuous analysis of the octane level provides an indication of the deactivation of the solid alkylation catalyst over time. When the catalyst reaches maximum allowable deactivation, which is predetermined by setting a minimum allowable octane level, the reaction mixture is swung over to alkylation reactor 2 where the alkylation process is continued. As the alkylation process continues in the alkylation reactor 2, the catalyst in the alkylation reactor 1 is regenerated.

In an alkylation process which uses a solid alkylation catalyst, it is preferable that the alkylation reaction takes place above 20° C. and below the lowest critical temperature amongst the reactants such that the reaction components will be maintained in liquid phase. Preferably, the reaction takes place at a temperature of between about 20° and 100° C. It is also preferable that the olefins have a reactor residence time of between about 0.1 and 300 minutes, more preferably about 2–20 minutes. The pressure in the reactor is desirably at a pressure which is high enough to maintain the reactants in liquid phase. The reaction mixture preferably includes an excess of isobutane, ranging about 10 to 100 mole/mole of olefin feed.

The alkylation catalyst which is used in this invention is a solid alkylation catalyst. Materials typical of solid alkylation catalysts are solid acid catalysts. Preferably, the solid alkylation catalyst is a zeolite, for example an alumina silicate, or a silicoaluminophosphate such as that disclosed by B. M. Lok et al. in "Silicoaluminophosphate Molecular Sieves: Another New Class of Microporous Crystalline Inorganic Solids", J. Am. Chem. Soc. 1984, (106) 6092–6093. Particularly useful molecular sieves are the larger pore materials such as zeolite Y.

The solid acid catalyst can be admixed with a variety of binder materials and the mixture used as the alkylation catalyst. The binder materials can include porous, refractory alumina compounds such as gamma alumina, bentonite clay, diatomaceous earth, silica, magnesia, zirconia, thoria, and the like.

On completion of the on-oil portion of the alkylation process, carbonaceous material which has been deposited on the alkylation catalyst as a result of the alkylation reaction is reacted by heating the solid alkylation catalyst in the presence of ozone. Preferably, the ozone is an ozone vapor stream which includes ozone at a concentration of about 1–50 Vol. %, with the remainder of the ozone stream being a relatively inert vapor such as air or oxygen. More preferably the ozone in the ozone stream is at a concentration of about 3–10 Vol. %. It is also preferable that the ozone stream have a gas rate of about 5–500 Standard Cubic Feet (SCF)/Hour/lb.Cat., more preferably about 5–75 SCF/Hour/lb.Cat.

Reaction of the carbonaceous material is not particularly dependent upon pressure. It is preferable, however, that the reaction pressure be between about 0 and 1000 psig. More preferably, the reaction pressure will be about 0–250 psig.

The carbonaceous material should be reacted at a temperature which will not adversely affect catalyst activity. Lower regeneration temperatures are particularly desirable. For example, a temperature range of about 20°–200° C. is preferred, with a range of about 20°–150° C. being more preferable.

Upon reacting the carbonaceous material, an ozonated hydrocarbon product is formed. An ozonated hydrocarbon is considered to be a hydrocarbon which is typically formed as a product of a combustion process. The ozonated hydrocarbon product which forms in this reaction process will include compounds having carbonyl carbons. As is well known in the art, carbonyl carbons are carbons which are double bonded to oxygen. For example, groups which have carbonyl carbons include aldehydes, ketones, carboxylic acids, amides and esters.

After the adsorbed carbonaceous material is reacted to form ozonated hydrocarbon, the carbonyl carbons within the ozonated hydrocarbon are desorbed from the solid alkylation catalyst. Desorbing the carbonyl carbons will effectively remove the ozonated hydrocarbon from the solid alkylation catalyst. By desorbing the carbonyl carbons in a step separate from the step of reacting the adsorbed carbonaceous material to form an ozonated hydrocarbon product, the entire regeneration process can be performed at lower overall temperatures compared to the known processes. A benefit of the lower regeneration temperatures is that a high catalyst activity can be maintained for significantly longer periods of time. Overall regeneration time and energy consumption can also be reduced.

The carbonyl components are preferably desorbed by sweeping the catalyst with a desorption fluid. The desorption fluid can be an inert gas such as nitrogen, helium, argon or the like; a refinery gas containing hydrogen, methane or hydrocarbons such as refinery fuel gas, reformer make gas, atmospheric and vacuum unit light ends, and fluidized catalytic cracking unit light ends; air; a liquid such as an aromatic containing stream, e.g., reformate, benzene, toluene and xylenes; or an oxygenate such as alcohols (e.g., ethanol, glycol, and methanol), ethers and esters. Alternatively, the catalyst can be swept by placing the catalyst under a vacuum.

It is preferable that the carbonyl carbons be desorbed at a temperature of at least about 80° C., preferably at a temperature of about 150°-300° C. The catalyst is considered to be effectively desorbed of carbonyl carbons when a photoacoustic infrared spectrum indicates essentially an absence of a carbonyl peak at about 1530-2000 cm$^{-1}$, preferably about 1590-1750 cm$^{-1}$. Effective desorption is also demonstrated when the level of oxygenates is less than about 500 ppm.

The invention will be more fully understood by reference to the following examples and comparative data illustrating its more salient features. All parts are given in terms of weight except as otherwise specified. It should also be noted that the specific examples are for purposes of illustration and should not be used to further define the invention from what is claimed.

EXAMPLE 1

Alkylation was carried out in a fixed-bed pilot plant at 80°-84° C. and 400 psig. A 39:1 mole/mole mix of isobutane and butylenes was reacted over an ultrastable Y zeolite (LZY-82, Union Carbide), supplied by UOP, at a rate of 0.27 cc of butylenes per gram of catalyst per hour. The reactor effluent was collected in a pressurized cylinder. Unreacted isobutane and butylenes were separated from the liquid product, $C_5+$, in a debutanizer and analyzed by gas chromatography/mass spectrometry techniques.

Table 1 summarizes the experimental conditions and product quality for a fresh catalyst. A total of 0.21 cc of butylenes were processed per gram of the catalyst. In that time, the average conversion of butylenes was 93.8%. The reaction was highly selective for alkylation, resulting in a $C_5+$ yield of 2.1 gms per gm of butylenes fed to the reactor. The $C_5+$ liquid contained 54.0 wt. % of $C_8$ paraffins, which indicates a high octane rating and that the catalyst was capable of alkylating butylenes with isobutane at moderate conditions.

TABLE 1

| Catalyst | Ultrastable Y zeolite |
|---|---|
| Description | Fresh |
| Feed | Isobutane/butylenes (39:1 mole/mole) |
| Operation: | |
| Pressure, psig | 400 |
| Feed Rate, cc/gm/hr (Butylenes) | 0.27 |
| Temp °C. (Avg.) | 83.2 |
| Butylenes Processed (cc/gm of catalyst) | 0-0.21 |
| Product Quality | |
| Butylene Conversion, Wt. % | 93.8 |
| $C_5+$ Yield, gms/gm Butylene Fed | 2.1 |
| $C_8$ Paraffins in Liquid, Wt. % | 54.0 |

EXAMPLE 2

Alkylation was carried out as in Example 1, except that the run time for the fresh catalyst, Run A of Table 2, was about two times longer than in Example 1. As expected, due to the longer run time, butylene conversion declined from 93.8% (Example 1) to 85.5%, and $C_5+$ alkylate yield declined from 2.1 to 1.8 gms per gm of butylene feed. This catalyst, nevertheless, remained quite effective for alkylation.

The spent catalyst from Run A had a carbon level of 4.7 wt. % as determined by Leco (ASTM D5291-92). The spent catalyst was regenerated with ozone in a fixed-bed mode, simulating the process scheme of FIG. 1. Ozone was produced using a lab ozonator (manufactured by Oztec), which was fed with oxygen. The resultant ozone stream was passed over the catalyst, which was maintained at 90°-110° C. After approximately 13 hours of treatment, the carbon level on the catalyst was reduced to 0.5 wt. %. The catalyst was then desorbed overnight by sweeping with air at 200° C.

After desorption, the catalyst was run again using parameters significantly close to that of Run A. This run was designated as Run B. The specific conditions are listed in Table 2. Over a similar duration of run time, as indicated by the volume of butylenes processed (cc/gm of catalyst), the catalyst activity and selectivity in Run A and Run B (butylene conversion, $C_5+$ yield, and $C_8$ content) were also significantly close.

TABLE 2

| Run | A | B |
|---|---|---|
| Catalyst | Ultrastable Y zeolite | |
| Description | Fresh | Catalyst from Run A regenerated with Ozone plus desorption step |
| Feed | Isobutane/butylene (39:1 mole/mole) | |
| Operation | | |
| Pressure, psig | 400 | |
| Feed Rate cc/gm/hr (Butylenes) | 0.27 | |
| Temp, °C. | 81.8 | 82.3 |
| Butylenes Processed (cc/gm of catalyst) | 0.07-0.48 | 0.1-0.51 |
| Product Quality | | |
| Butylene Conversion, Wt. % | 85.5 | 89.8 |
| $C_5+$ Yield, gm/gm Butylene Fed | 1.8 | 1.9 |
| $C_8$ Paraffins in Liquid, Wt. % | 56.7 | 52.5 |

EXAMPLE 3 (COMPARATIVE)

Fresh ultrastable Y zeolite was run as in Example 1. The run duration for the fresh catalyst, Run C, was similar to that in Example 1. The run data are shown in Table 3. Butylene conversion was 90.0% with good selectivity for alkylation, as indicated by the high $C_5+$ yield of 2.2 gms/gm of olefin fed to the unit. $C_8$ paraffin content in the $C_5+$ alkylate was 56.9 wt. %. The spent catalyst from Run C indicated a carbon level of 4.3 wt. %.

The catalyst from Run C was regenerated with ozone, reducing the carbon level to 0.5 wt. %; a level similar to that upon regeneration in Example 2. The regenerated catalyst was then tested for alkylation activity in Run D (Table 3). The results of this test show that there was a significant decline in conversion and $C_5+$ yield compared to the fresh catalyst as well as compared to the ozone regenerated catalyst that had been desorbed in air at 200° C. (Run B, Example 2).

TABLE 3

| Run | C | D |
|---|---|---|
| Catalyst | Ultrastable Y Zeolite | |
| Description | Fresh | Catalyst from Run C regenerated with Ozone only |
| Feed | Isobutane/butylenes (39:1 mole/mole) | |
| Operation | | |
| Pressure, psig | 400 | |
| Feed Rate, cc/gm/hr (Butylenes) | 0.27 | |
| Temp, °C. | 82.9 | 80.4 |
| Butylenes Processed | 0.07-0.21 | 0.08-0.35 |

TABLE 3-continued

| Run | C | D |
|---|---|---|
| (cc/gm of Catalyst) | | |
| Product Quality | | |
| Butylenes Conversion, Wt. % | 90.0 | 77 |
| C$_5$+ Yield, gm/gm Butylene Fed | 2.2 | 1.5 |
| C$_8$ Paraffins in Liquid, Wt. % | 56.9 | 47.6 |

EXAMPLE 4

Photoacoustic IR spectra of fresh ultrastable Y zeolite catalyst, catalyst regenerated with ozone and including the desorption step, and catalyst regenerated with ozone but without using the desorption step were compared. The photoacoustic IR spectra were obtained according to the approach described in *Fourier Transform IR Spectrometry*, Griffiths, P. R. et al., Chap. 9, Wiley-Interscience, New York 1988.

The photoacoustic IR spectra are shown in FIG. 2. A comparison of the spectra indicates that the desorbed catalyst has a photoacoustic IR spectrum that is significantly close to that of the fresh catalyst, whereas the catalyst that was not subjected to the desorption step shows a significant reduction in absorption at 1600–1700 wavenumbers (cm$^{-1}$). Absorption within this range is characteristic of carbonyls, e.g. ketones, aldehydes, carboxylic acids, etc.

Having now fully described this invention, it will be appreciated by those skilled in the art that the same can be performed within a wide range of equivalent parameters of composition and conditions without departing from the spirit or scope of the invention or any embodiment thereof.

What is claimed is:

1. A process for regenerating a molecular sieve alkylation catalyst having carbonaceous material adsorbed thereto, comprising:

heating the alkylation catalyst in the presence of ozone at a temperature between 20° C. and 200° C. for a time sufficient to react the carbonaceous material with the ozone to form ozonated hydrocarbons containing carbonyl carbons, and sweeping the heated alkylation catalyst with a desorption fluid at a temperature of 150°–300° C. for a time sufficient to effectively remove the ozonated hydrocarbons containing the carbonyl carbons and until a photoacoustic infrared spectrum indicates essentially an absence of a carbonyl peak at about 1530–2000 cm$^{-1}$.

2. The process of claim 1, wherein the desorption fluid is selected from the group consisting of an inert gas, a refinery gas, atmospheric light ends, vacuum unit light ends, fluid catalytic cracking light ends, air, an aromatic containing stream, alcohols, ethers, esters, and a vacuum stream.

3. The process of claim 1, wherein the ozone is an ozone vapor stream and contacts the solid alkylation catalyst at a rate of about 5–500 SCF/Hour/lb. Cat.

4. The process of claim 3, wherein the ozone vapor stream has an ozone concentration of about 1–50 Vol. %.

5. The process of claim 1, wherein the adsorbed carbonaceous material is reacted and the ozonated hydrocarbon is removed in a reaction vessel at a pressure of about 0–1000 psig.

6. The process of claim 1, wherein the alkylation catalyst comprises a zeolite catalyst.

7. In an alkylation process, wherein an olefin and a branched chain paraffin are contacted together with a molecular sieve alkylation catalyst to form an alkylate product with carbonaceous material being adsorbed to the alkylation catalyst, the improvement comprising:

stopping the olefin and branched chain paraffin from contacting the alkylation catalyst, heating the alkylation catalyst in the presence of ozone at a temperature between 20° C. and 200° C. for a time sufficient to react the carbonaceous material with the ozone to form ozonated hydrocarbons containing carbonyl carbons, sweeping the heated alkylation catalyst with a desorption fluid at a temperature of 150°–300° C. for a time sufficient to effectively remove the ozonated hydrocarbons containing the carbonyl carbons and until a photoacoustic infrared spectrum indicates essentially an absence of a carbonyl peak at about 1530–2000 cm$^{-1}$, and recontacting the olefin and branched chain paraffin with the regenerated alkylation catalyst to form alkylate product.

8. The process of claim 7, wherein the desorption fluid is selected from the group consisting of an inert gas, a refinery gas, atmospheric light ends, vacuum unit light ends, fluid catalytic cracking light ends, air, an aromatic containing stream, alcohols, ethers, esters, and a vacuum stream.

9. The process of claim 7, wherein the ozone is an ozone vapor stream and contacts the solid alkylation catalyst at a rate of about 5–500 SCF/Hour/lb.Cat.

10. The process of claim 9, wherein the ozone vapor stream has an ozone concentration of about 1–50 Vol. %.

11. The process of claim 7, wherein the adsorbed carbonaceous material is reacted and the ozonated hydrocarbon is removed in a reaction vessel at a pressure of about 0–1000 psig.

12. The process of claim 7, wherein the alkylation catalyst comprises a zeolite catalyst.

* * * * *